United States Patent
Proulx-Lafrance et al.

(10) Patent No.: US 8,283,471 B2
(45) Date of Patent: Oct. 9, 2012

(54) SUCCINATE SALT OF 2-((4-(1-METHYL-4-PYRIDIN-4-YL)-1H-PYRAZOL-3-YL)PHENOXY)METHYL)QUINOLINE

(75) Inventors: Caroline Proulx-Lafrance, Ledyard, CT (US); Patrick Robert Verhoest, Old Lyme, CT (US)

(73) Assignee: Pfizer, Inc., New York, NY (US)

( * ) Notice: Subject to any disclaimer, the term of this patent is extended or adjusted under 35 U.S.C. 154(b) by 501 days.

(21) Appl. No.: 12/515,612

(22) PCT Filed: Dec. 3, 2007

(86) PCT No.: PCT/IB2007/003819
§ 371 (c)(1),
(2), (4) Date: May 20, 2009

(87) PCT Pub. No.: WO2008/084299
PCT Pub. Date: Jul. 17, 2008

(65) Prior Publication Data
US 2010/0063089 A1    Mar. 11, 2010

Related U.S. Application Data

(60) Provisional application No. 60/871,260, filed on Dec. 21, 2006.

(51) Int. Cl.
*C07D 215/12* (2006.01)
*A61K 31/4709* (2006.01)

(52) U.S. Cl. .................................. 546/176; 514/314
(58) Field of Classification Search .................. 514/314; 546/176
See application file for complete search history.

(56) References Cited

U.S. PATENT DOCUMENTS

| | | | | |
|---|---|---|---|---|
| 5,795,909 | A  * | 8/1998 | Shashoua et al. | 514/449 |
| 6,844,349 | B2 * | 1/2005 | Kath et al. | 514/266.21 |
| 2003/0045583 | A1 * | 3/2003 | Hadfield et al. | 514/649 |
| 2003/0149044 | A1 * | 8/2003 | Quallich et al. | 514/249 |
| 2006/0281759 | A1 * | 12/2006 | de Diego et al. | 514/255.03 |
| 2007/0149552 | A1 * | 6/2007 | Ku et al. | 514/259.31 |

FOREIGN PATENT DOCUMENTS
WO    2006078828    7/2006
* cited by examiner

*Primary Examiner* — Jennifer M Kim
(74) *Attorney, Agent, or Firm* — J. Michael Dixon

(57) ABSTRACT

The present invention relates to a succinate salt of 2-((4-(1-methyl-4-(pyridin-4-yl)-1H-pyrazol-3-yl)phenoxy)methyl)quinoline, and to a method for treating disorders of the Central Nervous System (CNS) and other disorders in a mammal, including a human, by administering to the mammal the succinate salt. It also relates to pharmaceutical compositions containing a pharmaceutically acceptable carrier and the succinate salt.

9 Claims, 1 Drawing Sheet

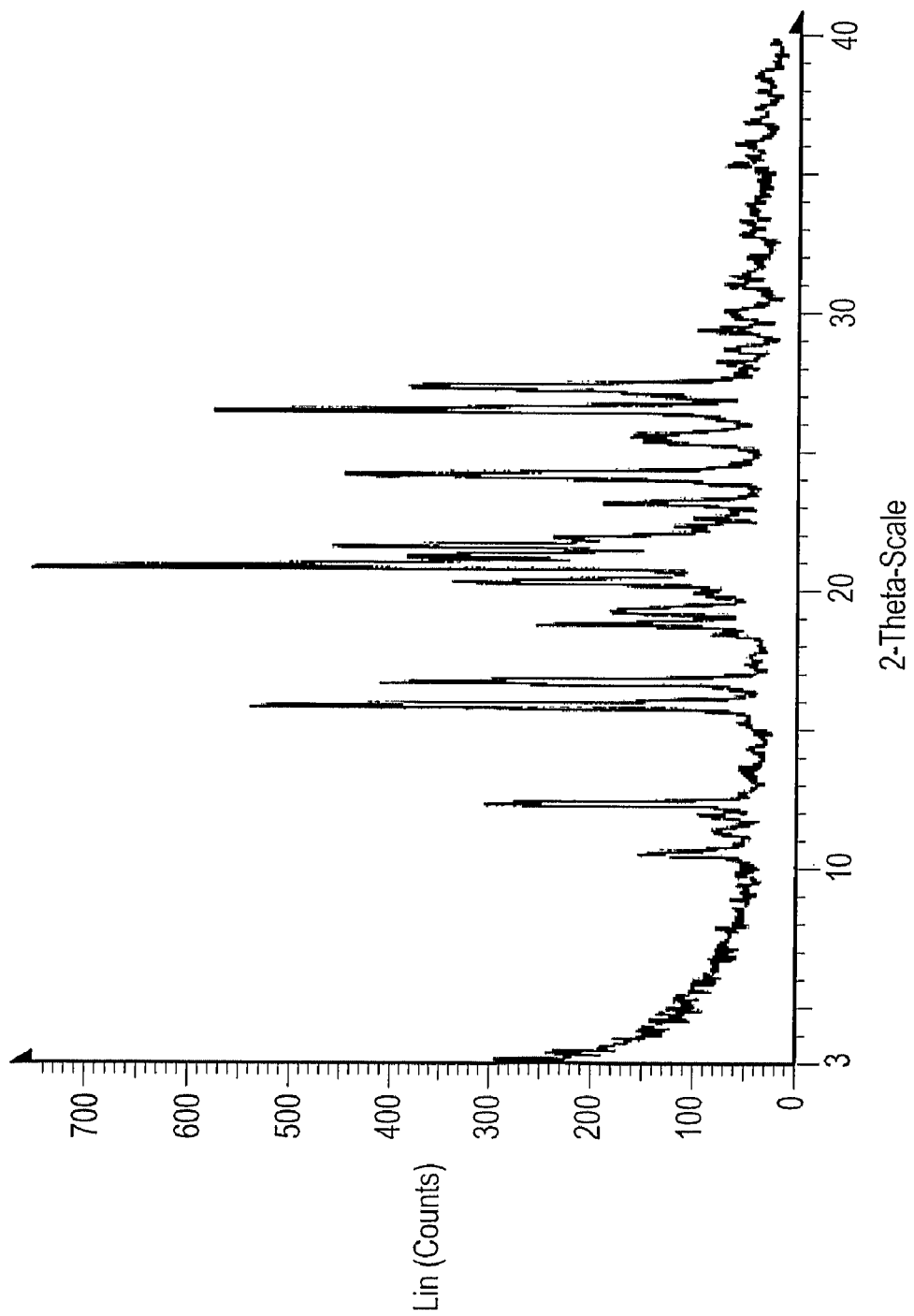

SUCCINATE SALT OF 2-((4-(1-METHYL-4-PYRIDIN-4-YL)-1H-PYRAZOL-3-YL)PHENOXY)METHYL)QUINOLINE

FIELD OF THE INVENTION

The present invention relates to a succinate salt of 2-((4-(1-methyl-4-(pyridin-4-yl)-1H-pyrazol-3-yl)phenoxy)methyl)quinoline, and to a method for treating disorders of the Central Nervous System (CNS) and other disorders in a mammal, including a human, by administering to the mammal the succinate salt. It also relates to pharmaceutical compositions containing a pharmaceutically acceptable carrier and the succinate salt.

BACKGROUND OF THE INVENTION

Phosphodiesterases (PDEs) are a class of intracellular enzymes involved in the hydrolysis of the nucleotides cyclic adenosine monophosphate (cAMP) and cyclic guanosine monophosphate (cGMP) into their respective nucleotide monophosphates. The cyclic nucleotides cAMP and cGMP are synthesized by adenylyl and guanylyl cyclases, respectively, and serve as secondary messengers in several cellular pathways.

The cAMP and cGMP function as intracellular second messengers regulating a vast array of intracellular processes particularly in neurons of the central nervous system. In neurons, this includes the activation of cAMP and cGMP-dependent kinases and subsequent phosphorylation of proteins involved in acute regulation of synaptic transmission as well as in neuronal differentiation and survival. The complexity of cyclic nucleotide signaling is indicated by the molecular diversity of the enzymes involved in the synthesis and degradation of cAMP and cGMP. There are at least ten families of adenylyl cyclases, two of guanylyl cyclases, and eleven of phosphodiesterases. Furthermore, different types of neurons are known to express multiple isozymes of each of these classes, and there is good evidence for compartmentalization and specificity of function for different isozymes within a given neuron.

A principal mechanism for regulating cyclic nucleotide signaling is by phosphodiesterase-catalyzed cyclic nucleotide catabolism. There are 11 known families of PDEs encoded by 21 different genes. Each gene typically yields multiple splice variants that further contribute to the isozyme diversity. The PDE families are distinguished functionally based on cyclic nucleotide substrate specificity, mechanism(s) of regulation, and sensitivity to inhibitors. Furthermore, PDEs are differentially expressed throughout the organism, including in the central nervous system. As a result of these distinct enzymatic activities and localization, different PDEs' isozymes can serve distinct physiological functions. Furthermore, compounds that can selectively inhibit distinct PDE families or isozymes may offer particular therapeutic effects, fewer side effects, or both.

PDE10 is identified as a unique family based on primary amino acid sequence and distinct enzymatic activity. Homology screening of EST databases revealed mouse PDE10A as the first member of the PDE10 family of PDEs (Fujishige et al., J. Biol. Chem. 274:18438-18445, 1999; Loughney, K. et al., Gene 234:109-117, 1999). The murine homologue has also been cloned (Soderling, S. et al., Proc. Natl. Acad. Sci. USA 96:7071-7076, 1999) and N-terminal splice variants of both the rat and human genes have been identified (Kotera, J. et al., Biochem. Biophys. Res. Comm. 261:551-557, 1999; Fujishige, K. et al., Eur. J. Biochem. 266:1118-1127, 1999). There is a high degree of homology across species. The mouse PDE10A1 is a 779 amino acid protein that hydrolyzes both cAMP and cGMP to AMP and GMP, respectively. The affinity of PDE10 for cAMP (Km=0.05 μM) is higher than for cGMP (Km=3 μM). However, the approximately 5-fold greater Vmax for cGMP over cAMP has lead to the suggestion that PDE10 is a unique cAMP-inhibited cGMPase (Fujishige et al., J. Biol. Chem. 274:18438-18445, 1999).

The PDE 10 family of polypeptides shows a lower degree of sequence homology as compared to previously identified PDE families and has been shown to be insensitive to certain inhibitors that are known to be specific for other PDE families. U.S. Pat. No. 6,350,603, incorporated herein by reference.

PDE10 also is uniquely localized in mammals relative to other PDE families. mRNA for PDE10 is highly expressed only in testis and brain (Fujishige, K. et al., Eur J Biochem. 266:1118-1127, 1999; Soderling, S. et al., Proc. Natl. Acad. Sci. 96:7071-7076, 1999; Loughney, K. et al., Gene 234:109-117, 1999). These initial studies indicated that within the brain PDE10 expression is highest in the striatum (caudate and putamen), n. accumbens, and olfactory tubercle. More recently, a detailed analysis has been made of the expression pattern in rodent brain of PDE10 mRNA (Seeger, T. F. et al., Abst. Soc. Neurosci. 26:345.10, 2000) and PDE10 protein (Menniti, F. S., Stick, C. A., Seeger, T. F., and Ryan, A. M., Immunohistochemical localization of PDE10 in the rat brain. William Harvey Research Conference 'Phosphodiesterase in Health and Disease', Porto, Portugal, Dec. 5-7, 2001).

A variety of therapeutic uses for PDE inhibitors has been reported including obtrusive lung disease, allergies, hypertension, angina, congestive heart failure, depression and erectile dysfunction (WO 01/41807 A2, incorporated herein by reference).

BRIEF DESCRIPTION OF THE DRAWINGS

FIG. 1 is the X-ray powder diffraction pattern of the succinate salt of 2-((4-(1-methyl-4-(pyridin-4-yl)-1H-pyrazol-3-yl)phenoxy)methyl)quinoline.

SUMMARY OF THE INVENTION

The present invention provides a succinate salt of 2-((4-(1-methyl-4-(pyridin-4-yl)-1H-pyrazol-3-yl)phenoxy)methyl)quinoline, ("succinate salt"), which is represented by Formula I:

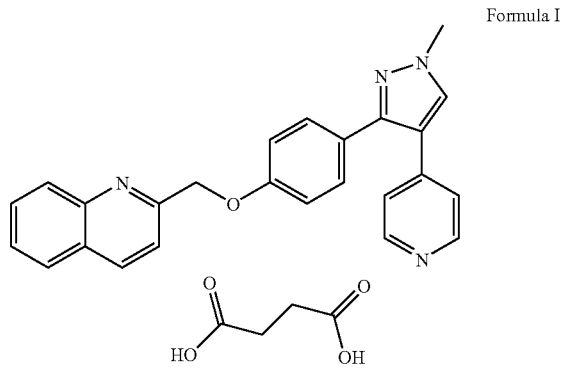

Formula I

Another name for the quinoline compound in formula I is 2-[4-(1-Methyl-4-pyridin-4-yl-1H-pyrazol-3-yl)-phenoxymethyl]-quinoline. Succinate salts, in general, may also be known as succinic acid salts.

The succinate salt of the present invention is a PDE10 inhibitor useful in the treatment of schizophrenia and other CNS diseases.

DETAILED DESCRIPTION OF THE INVENTION

In the present invention, the term "salt" or "succinate salt" is meant to encompass all solid state forms containing succinic acid and the quinoline compound (formula 1) associated in the solid state including by ionic bonds and/or hydrogen bonds.

In the course of drug development, it is generally assumed to be important to discover the most stable crystalline form of the drug. This most stable crystalline form is the form which is likely to have the best chemical stability, and thus the longest shelf-life in a formulation. The search for the most stable form is arduous and the outcome is unpredictable.

As used herein, "crystalline" means a material that has an ordered, long range molecular structure. The degree of crystallinity of a crystal form can be determined by many techniques including, for example, powder X-ray diffraction, moisture sorption, differential scanning calorimetry, solution calorimetry, polarized light microscopy and dissolution properties.

Crystalline organic compounds consist of a large number of atoms that are arranged in a periodic array in three-dimensional space. The structural periodicity normally manifests distinct physical properties, such as sharp, explicit spectral features by most spectroscopic probes (e.g., X-ray diffraction, infrared and solid state NMR). X-ray diffraction (XRD) is acknowledged to be one of the most sensitive methods to determine the crystallinity of solids. Crystals yield explicit diffraction maxima that arise at specific angles consistent with the lattice interplanar spacings, as predicted by Bragg's law. On the contrary, amorphous materials do not possess long-range order. They often retain additional volume between molecules, as in the liquid state. Amorphous solids normally unveil a featureless XRD pattern with broad, diffuse halos because of the absence of the long range order of repeating crystal lattice.

Powder X-ray diffraction, (PXRD) has reportedly been used to characterize different crystal forms of organic compounds (e.g., compounds useful in pharmaceutical compositions). See, for example, U.S. Pat. Nos. 5,504,216 (Holohan et al), 5,721,359 (Dunn et al.), 5,910,588 (Wangnick et al.), 6,066,647 (Douglas et al.), 6,225,474 (Matsumoto et al.), 6,239,141 (Allen et al.), 6,251,355 (Murata et al.), 6,288,057 (Harkness), 6,316,672 (Stowell et al.), and 6,329,364 (Groleau).

Crystalline materials are preferred in many pharmaceutical applications. Crystalline forms are generally thermodynamically more stable than amorphous forms of the same substance. This thermodynamic stability is preferably reflected in the lower solubility and improved physical stability of the crystalline form. The regular packing of the molecules in the crystalline solid preferably denies the incorporation of chemical impurities. Hence crystalline materials generally possess higher chemical purity than their amorphous counterparts. The packing in the crystalline solid generally constrains the molecules to well defined lattice positions and reduces the molecular mobility that is the prerequisite for chemical reactions. Hence, crystalline solids, with very few notable exceptions, are chemically more stable than amorphous solids of the same molecular composition.

The crystalline form of the crystalline polymorph of the succinate salt of the present invention has the powder X-ray diffraction profile provided in FIG. 1. Characteristic diffraction peaks as used herein are unique peaks to identify the form. Preferably, the characteristic peaks are selected from about 20 of the most intense peaks, more preferably from about 10 of the most intense peaks, and most preferably from about 3 to 5 of the most intense peaks in the diffraction pattern.

For a drug form to be practically useful for human or animal therapy, it is also desirable that the drug form to be non-deliquescent, and more particularly, exhibit minimal hygroscopicity. Dosage forms containing highly hygroscopic drugs require protective packaging, and may exhibit altered dissolution if stored in a humid environment. Thus it is desirable to identify non-hygroscopic crystalline salts of a drug.

A drug, crystalline or non-crystalline, may exist in an anhydrous form, or as a hydrate or solvate or hydrate/solvate. The hydration state and solvation state of a drug affects its solubility and dissolution behavior. The term 'solvate' is used herein to describe the association in the solid state of an active pharmaceutical ingredient (API) molecule and a solvent molecule. Typically the solvent molecule incorporated in the solid state crystal lattice that used to crystallize the API from solution but is not limited to this method of preparation. The term "hydrate" is employed when said solvent is water.

The melting point is also an important physical aspect in the manufacture of a drug. In order to permit manufacture of tablets on commercial tablet presses, it is desirable that the drug melting point be greater than around 60° C., preferably greater than 100° C., more preferably greater than 120° C. to prevent drug melting during tablet manufacture. A preferred drug form in this instance is one that has the highest melting point. In addition, it is desirable to have a high melting point to assure chemical stability of solid drug in a solid dosage form at high environmental storage temperatures which occur in direct sunlight and in geographic areas such as near the equator It has been discovered that succinate salt of 2-((4-(1-methyl-4-(pyridin-4-yl)-1H-pyrazol-3-yl)phenoxy)methyl) quinoline has the advantage of possessing the required properties to enable it to be formulated as a pharmaceutical. Namely, it is not deliquescent, it has a high melting point, it is non-hygroscopic, and it is crystalline in form.

The succinate salt of Formula I may exist in different polymorphic forms, all of which are encompassed by the present invention.

The present invention includes all pharmaceutically acceptable isotopically-labelled compounds of the salt of 2-((4-(1-methyl-4-(pyridin-4-yl)-1H-pyrazol-3-yl)phenoxy) methyl)quinoline, wherein one or more atoms are replaced by atoms having the same atomic number, but an atomic mass or mass number different from the atomic mass or mass.

The succinate salt of Formula I of the present invention encompasses the anhydrous form and solvates or hydrates thereof. The salt may form solvates or hydrates with solvents such as, but not limited to, water, acetone, and alcohol such as ethanol, propanol, butanol, propylene glycol, etc.

Preferably, the succinate salt of Formula I is anhydrous.

In an embodiment of the present invention, the succinate salt has characteristic X-ray powder diffraction peaks as measured with copper radiation of 2-Theta±0.1° of 12.2, 15.8, 16.7, 21.0, 24.2 and/or 26.6.

In another embodiment, the succinate salt has characteristic X-ray powder diffraction peaks as measured with copper radiation of 2-Theta±0.1° of 15.8, 21.0 and 26.6.

In another embodiment, the succinate the salt has characteristic X-ray powder diffraction peaks as measured with copper radiation of 2-Theta±0.1° of 15.8, 16.7, 21.0, 24.2 and 26.6.

In another embodiment, the succinate salt of Formula I has the characteristic X-ray powder diffraction pattern of FIG. 1.

In a further embodiment, the succinate salt of Formula I has a melting onset temperature of 184±3° C.

In another embodiment, the succinate salt increases in weight by less than 0.5% at 90±2% relative humidity in an isothermal (25.1±0.1° C.) moisture sorption test conducted from approximately 1% to 90% (±2%) humidity.

The present invention relates to a pharmaceutical composition comprising the succinate salt of Formula I, and a pharmaceutically acceptable carrier. Preferably, the succinate salt of the pharmaceutical composition is crystalline.

This invention also pertains to a pharmaceutical composition for treatment of certain psychotic disorders and conditions such as schizophrenia, delusional disorders and drug induced psychosis; to anxiety disorders such as panic and obsessive-compulsive disorder; and to movement disorders including Parkinson's disease and Huntington's disease, comprising an amount of a succinate salt of formula I effective in inhibiting PDE 10.

The term "inhibiting PDE 10", as used herein, means the prevention or therapeutically significant reduction in PDE10 activity. One of ordinary skill in the art is readily able to determine whether a compound inhibits PDE10 activity. For example, assays which may conveniently be used in order to assess the PDE10 inhibition may be found is U.S. Patent Application Publication No. 2006/0154931 (U.S. Ser. No. 11/326,221) published on Jul. 13, 2006, herein incorporated by reference in its entirety.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

In another embodiment, this invention relates to a pharmaceutical composition for treating psychotic disorders and condition such as schizophrenia, delusional disorders and drug induced psychosis; anxiety disorders such as panic and obsessive-compulsive disorder; and movement disorders including Parkinson's disease and Huntington's disease, comprising an amount of a succinate salt of formula I effective in treating said disorder or condition.

Examples of psychotic disorders that can be treated according to the present invention include, but are not limited to, schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type.

Examples of movement disorders that can be treated according to the present invention include but are not limited to selected from Huntington's disease and dyskinesia associated with dopamine agonist therapy, Parkinson's disease, restless leg syndrome, and essential tremor.

Other disorders that can be treated according to the present invention are obsessive/compulsive disorders, Tourette's syndrome and other tic disorders.

In another embodiment, this invention relates to a method for treating an anxiety disorder or condition in a mammal which method comprises administering to said mammal an amount of a succinate salt of formula I effective in inhibiting PDE 10.

This invention also provides a method for treating an anxiety disorder or condition in a mammal which method comprises administering to said mammal an amount of a succinate salt of formula I effective in treating said disorder or condition.

Examples of anxiety disorders that can be treated according to the present invention include, but are not limited to, panic disorder; agoraphobia; a specific phobia; social phobia; obsessive-compulsive disorder; post-traumatic stress disorder; acute stress disorder; and generalized anxiety disorder.

This invention further provides a method of treating a drug addiction, for example an alcohol, amphetamine, cocaine, or opiate addiction, in a mammal, including a human, which method comprises administering to said mammal an amount of a succinate salt of formula I effective in treating drug addiction.

This invention also provides a method of treating a drug addiction, for example an alcohol, amphetamine, cocaine, or opiate addiction, in a mammal, including a human, which method comprises administering to said mammal an amount of a succinate salt of formula I effective in inhibiting PDE10.

A "drug addiction", as used herein, means an abnormal desire for a drug and is generally characterized by motivational disturbances such a compulsion to take the desired drug and episodes of intense drug craving.

This invention further provides a method of treating a disorder comprising as a symptom a deficiency in attention and/or cognition in a mammal, including a human, which method comprises administering to said mammal an amount of a succinate salt of formula I effective in treating said disorder.

This invention also provides a method of treating a disorder or condition comprising as a symptom a deficiency in attention and/or cognition in a mammal, including a human, which method comprises administering to said mammal an amount of a succinate salt of formula I effective in inhibiting PDE10.

This invention also provides a method of treating a disorder or condition comprising as a symptom a deficiency in attention and/or cognition in a mammal, including a human, which method comprises administering to said mammal an amount of a succinate salt of formula I effective in treating said disorder or condition.

The phrase "deficiency in attention and/or cognition" as used herein in "disorder comprising as a symptom a deficiency in attention and/or cognition" refers to a subnormal functioning in one or more cognitive aspects such as memory, intellect, or learning and logic ability, in a particular individual relative to other individuals within the same general age population. "Deficiency in attention and/or cognition" also refers to a reduction in any particular individual's functioning in one or more cognitive aspects, for example as occurs in age-related cognitive decline.

Examples of disorders that comprise as a symptom a deficiency in attention and/or cognition that can be treated according to the present invention are dementia, for example Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline.

This invention also provides a method of treating a mood disorder or mood episode in a mammal, including a human, comprising administering to said mammal an amount of a succinate salt of formula I effective in treating said disorder or episode.

This invention also provides a method of treating a mood disorder or mood episode in a mammal, including a human, comprising administering to said mammal an amount of a succinate salt of formula I effective in inhibiting PDE10.

Examples of mood disorders and mood episodes that can be treated according to the present invention include, but are not limited to, major depressive episode of the mild, moderate or severe type, a manic or mixed mood episode, a hypomanic mood episode; a depressive episode with atypical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder.

This invention further provides a method of treating a neurodegenerative disorder or condition in a mammal, including a human, which method comprises administering to said mammal an amount of a succinate salt of formula I effective in treating said disorder or condition.

This invention further provides a method of treating a neurodegenerative disorder or condition in a mammal, including a human, which method comprises administering to said mammal an amount of a succinate salt of formula I effective in inhibiting PDE10.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can be treated according to the present invention include, but are not limited to, Parkinson's disease; Huntington's disease; dementia, for example Alzheimer's disease, multi-infarct dementia, AIDS-related dementia, and Fronto temporal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy.

In one embodiment of the present invention, the neurodegenerative disorder or condition comprises neurodegeneration of striatal medium spiny neurons in a mammal, including a human.

In a further embodiment of the present invention, the neurodegenerative disorder or condition is Huntington's disease.

This invention also provides a pharmaceutical composition for treating psychotic disorders, delusional disorders and drug induced psychosis; anxiety disorders, movement disorders, mood disorders, neurodegenerative disorders and drug addiction, comprising an amount of a succinate salt of formula I effective in treating said disorder or condition.

This invention also provides a method of treating a disorder selected from psychotic disorders, delusional disorders and drug induced psychosis; anxiety disorders, movement disorders, mood disorders, and neurodegenerative disorders, which method comprises administering an amount of a succinate salt of formula I effective in treating said disorder.

This invention also provides a method of treating disorders selected from the group consisting of: dementia, Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; age-related cognitive decline, major depressive episode of the mild, moderate or severe type; a manic or mixed mood episode; a hypomanic mood episode; a depressive episode with atypical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder comprising a delusional disorder or schizophrenia; a bipolar disorder comprising bipolar I disorder, bipolar II disorder, cyclothymic disorder, Parkinson's disease; Huntington's disease; dementia, Alzheimer's disease, multi-infarct dementia, AIDS-related dementia, Fronto temporal Dementia; neurodegeneration associated with cerebral trauma; neurodegeneration associated with stroke; neurodegeneration associated with cerebral infarct; hypoglycemia-induced neurodegeneration; neurodegeneration associated with epileptic seizure; neurodegeneration associated with neurotoxin poisoning; multi-system atrophy, paranoid, disorganized, catatonic, undifferentiated or residual type; schizophreniform disorder; schizoaffective disorder of the delusional type or the depressive type; delusional disorder; substance-induced psychotic disorder, psychosis induced by alcohol, amphetamine, cannabis, cocaine, hallucinogens, inhalants, opioids, or phencyclidine; personality disorder of the paranoid type; and personality disorder of the schizoid type.

This invention also provides a method of treating psychotic disorders, delusional disorders and drug induced psychosis; anxiety disorders, movement disorders, mood disorders, neurodegenerative disorders and drug addiction which method comprises administering an amount of a succinate salt of formula I effective in inhibiting PDE10.

The succinate salt of Formula I of the present invention (hereinafter "the active compounds") can be administered via either the oral, transdermal (ea, through the use of a patch), intranasal, sublingual, rectal, parenteral or topical routes. Transdermal and oral administration are preferred. The active compounds are, most desirably, administered in dosages ranging from about 0.25 mg up to about 1500 mg per day, preferably from about 0.25 to about 300 mg per day in single or divided doses, although variations will necessarily occur depending upon the weight and condition of the subject being treated and the particular route of administration chosen. However, a dosage level that is in the range of about 0.01 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous solutions, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating so agents such as magnesium stearate, sodium lauryl sulfate and talc can be used for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active compound in a pharmaceutically acceptable oily or aqueous vehicle such as but not limited to sesame oil, peanut oil or aqueous propylene glycol, can be employed. The aqueous solutions should be suitably buffered, if necessary, and the liquid diluent first rendered isotonic. The preparation of the solutions is under sterile conditions and is readily accomplished by standard pharmaceutical techniques well known to those skilled in the art.

Parenteral administration may be by injection, including the intravenous, intraarticular, intramuscular, and subcutaneous forms. The aqueous solutions are suitable for intravenous injection purposes. The oily solutions are suitable for intraarticular, intramuscular and subcutaneous injection purposes.

It is also possible to administer the active compounds topically and this can be done by way of creams, a patch, jellies, gels, pastes, ointments and the like, in accordance with standard pharmaceutical practice.

Processes for making the free base compound may be found is U.S. Patent Application Publication No. 2006/0154931 (U.S. Ser. No. 11/326,221) published on Jul. 13, 2006, herein incorporated by reference in its entirety.

The following Examples illustrate the present invention. It is to be understood, however, that the invention, as fully described herein and as recited in the claims, is not intended to be limited by the details of the following Examples.

EXAMPLES

Example 1

Preparation of succinate salt of 2-((4-(1-methyl-4-(pyridin-4-yl)-1H-pyrazol-3-yl)phenoxy)methyl)quinoline To a solution of free base compound of 2-((4-(1-methyl-4-(pyridin-4-yl)-1H-pyrazol-3-yl)phenoxy)methyl)quinoline (3.0 g, 7.6 mmol) in ethyl acetate (75 ml) at 25° C. was added 900 mg (7.6 mmol) of succinic acid in 75 ml of ethyl acetate at 25° C. The mixture was stirred for 12 h at 25° C. The resulting precipitate was filtered, washes with diethyl ether and dried under vacuum to give 3.13 g of the title compound as white prism shaped crystals.

$^{1}$H-NMR: (400 MHz, $CD_3OD$) δ 8.38 (d, J=8.3 Hz, 1H), 8.32 (m, 2H), 8.03 (d, J=8.3 Hz, 1H), 8.00 (m, 1H), 7.94 (d, J=7.9 Hz, 1H), 7.75 (m, 1H), 7.74 (d, J=8.7 Hz, 1H), 7.60 (m, 1H), 7.35 (dd, J=8.7, 2.1 Hz, 2H), 7.28 (m, 2H), 7.10 (dd, J=8.7, 2.1 Hz, 2H), 5.37 (s, 2H), 3.93 (s, 3H), 2.54 (s, 4H);

$^{13}$C-NMR (100 MHz, $CD_3OD$) δ 175.0 158.9 157.9 149.5 148.6 147.2 142.8 137.9 132.0 130.2 130.0 128.0 127.9 127.8 126.9 125.9 122.7 119.6 117.2 114.9 70.7 37.9 28.7;

Elemental analysis calculated for anhydrous succinate salt C, 68.22; H, 5.13; N, 10.97. Found: C, 68.05; H, 4.99; N, 10.87. Melting Point: 184±3° C.

Method for collecting powder X-ray diffraction for succinate salt of 2-((4-(1-methyl-4-(pyridin-4-yl)-1H-pyrazol-3-yl)phenoxy)methyl)quinoline Powder X-Ray Diffraction (PXRD) Pattern Powder x-ray diffraction pattern was collected for the salt of Example 1 using a Bruker D5000 diffractometer (Madison Wis.) equipped with a copper radiation source, fixed slits (divergence 1.0 mm, antiscatter 1.0 mm, and receiving 0.6 mm) and a Kevex solid-state detector. Data was collected in the theta-two theta goniometer configuration from a flat plate sample holder at the Copper wavelength $Kα_1$=1.54056 and $Kα_2$=1.54439 (relative intensity 0.5) from 3.0 to 40.0 degrees two-theta using a step size of 0.040 degrees and a step time of one second. X-ray tube voltage and amperage were set at 40 kV and 30 mA respectively. Data were collected and analyzed using Bruker DIFFRAC Plus software. Samples were prepared by placing them in a quartz holder. (It is noted that a Bruker D5000 diffractometer is similar in operation to Siemans model D5000.) The results are summarized in Table 1 which provides the two-theta values and relative intensities for all of the reflections (lines) that have a relative intensity greater than or equal to 6% using a reflection width of 0.30 and a threshold of 1.0.

TABLE 1

Powder x-ray diffraction reflections for succinate salt of 2-((4-(1-methyl-4-(pyridin-4-yl)-1H-pyrazol-3-yl)phenoxy)methyl)quinoline (Example 1).

| Angle 2-Theta ± 0.2° | Relative Intensity* % |
|---|---|
| 10.5 | 20.6 |
| 11.3 | 11.6 |
| 11.8 | 13.0 |

TABLE 1-continued

Powder x-ray diffraction reflections for succinate salt of 2-((4-(1-methyl-4-(pyridin-4-yl)-1H-pyrazol-3-yl)phenoxy)methyl)quinoline (Example 1).

| Angle 2-Theta ± 0.2° | Relative Intensity* % |
|---|---|
| 12.2 | 40.6 |
| 13.5 | 8.7 |
| 14.3 | 9.8 |
| 15.8 | 71.6 |
| 16.7 | 54.6 |
| 17.6 | 6.5 |
| 18.4 | 11.8 |
| 18.8 | 33.7 |
| 19.2 | 24.2 |
| 19.9 | 14.2 |
| 20.3 | 44.8 |
| 21.0 | 100 |
| 21.3 | 51.2 |
| 21.6 | 61.2 |
| 21.9 | 29.5 |
| 22.3 | 16.1 |
| 22.6 | 13.9 |
| 23.2 | 25.5 |
| 24.2 | 59.7 |
| 25.4 | 20.2 |
| 25.6 | 22.0 |
| 26.6 | 76.9 |
| 27.4 | 19.4 |
| 27.2 | 24.7 |
| 27.4 | 51.1 |
| 28.3 | 11.0 |
| 28.8 | 10.2 |
| 29.4 | 13.6 |
| 30.1 | 9.8 |
| 31.1 | 9.8 |
| 31.4 | 10.3 |
| 32.1 | 7.1 |
| 32.9 | 8.1 |
| 33.3 | 8.1 |
| 35.4 | 9.8 |
| 37.0 | 7.7 |

*The relative intensity may vary depending on particle size and shape.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A succinate salt of Formula I:

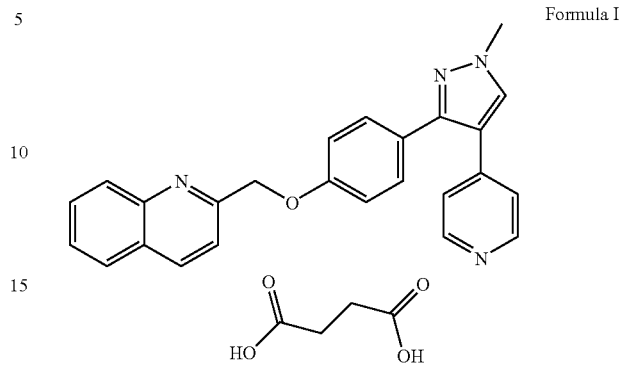

Formula I wherein the salt has characteristic X-ray powder diffraction peaks as measured with copper radiation of 2-Theta±0.1° of 15.8, 21.0 and 26.6.

2. The salt according to claim 1, wherein the salt has characteristic X-ray powder diffraction peaks as measured with copper radiation of 2-Theta±0.1° of 15.8, 16.7, 21.0, 24.2 and 26.6.

3. The salt according to claim 1, wherein the salt has a melting onset temperature of 184±3° C.

4. The salt according to claim 1, wherein the salt increases in weight by less than 0.5% at 90±2% relative humidity in an isothermal (25.1±0.1° C.) moisture sorption test conducted from approximately 1% to 90% (±2%) humidity.

5. The salt according to claim 1, wherein the salt is anhydrous.

6. A pharmaceutical composition comprising a succinate salt according to claim 1, and a pharmaceutically acceptable carrier.

7. A method of treating a disorder selected from psychotic disorders, delusional disorders and drug induced psychosis; anxiety disorders, movement disorders, mood disorders, and neurodegenerative disorders, which method comprises administering an amount of a succinate salt of claim 1 effective in treating said disorder.

8. A method of treating psychotic disorders, delusional disorders and drug induced psychosis; anxiety disorders, movement disorders, mood disorders, neurodegenerative disorders and drug addiction which method comprises administering an amount of the succinate salt of claim 1 effective in inhibiting PDE10.

9. A method of treating Huntington's Disease comprising administering an effective amount of a compound according to claim 1 to a patient in need thereof.

* * * * *